US010537272B2

(12) United States Patent
Bocquet et al.

(10) Patent No.: US 10,537,272 B2
(45) Date of Patent: Jan. 21, 2020

(54) DEVICE FOR MEASURING ELECTROPHYSIOLOGICAL DATA WITH IMPROVED RELIABILITY

(71) Applicant: IMPETO MEDICAL, Paris (FR)

(72) Inventors: Nicolas Bocquet, Chatillon (FR); Mathieu Seval, Villepreux (FR)

(73) Assignee: Impeto Medical, Paris (FR)

( * ) Notice: Subject to any disclaimer, the term of this patent is extended or adjusted under 35 U.S.C. 154(b) by 215 days.

(21) Appl. No.: 15/528,907

(22) PCT Filed: Nov. 25, 2015

(86) PCT No.: PCT/EP2015/077595
§ 371 (c)(1),
(2) Date: Aug. 31, 2017

(87) PCT Pub. No.: WO2016/083432
PCT Pub. Date: Jun. 2, 2016

(65) Prior Publication Data
US 2018/0085036 A1    Mar. 29, 2018

(30) Foreign Application Priority Data
Nov. 25, 2014  (FR) .................................... 14 61447

(51) Int. Cl.
*A61N 2/12*     (2006.01)
*A61N 2/00*     (2006.01)
(Continued)

(52) U.S. Cl.
CPC .......... *A61B 5/1495* (2013.01); *A61B 5/0002* (2013.01); *A61B 5/0531* (2013.01);
(Continued)

(58) Field of Classification Search
CPC .......... A61B 5/0531; A61B 2560/0276; A61B 2560/028; A61B 2560/0443;
(Continued)

(56) References Cited

U.S. PATENT DOCUMENTS 3,449,080 A    6/1969   Edwards
3,635,213 A    1/1972   LaHay
(Continued)

FOREIGN PATENT DOCUMENTS

FR    2912893 A1    8/2008
FR    2994819 A1    3/2014
(Continued)

OTHER PUBLICATIONS

Allen, John: "Topical Review; Photoplethysmography and its application in clinical physiological measurement," IOP Publishing, vol. 28, No. 3. Mar. 1, 2007, pp. R1-R39.
(Continued)

*Primary Examiner* — Christine H Matthews
*Assistant Examiner* — Joshua Daryl D Lannu
(74) *Attorney, Agent, or Firm* — Harness, Dickey & Pierce, PLC (57) ABSTRACT

A device for measuring electrophysiological data includes: a series of electrodes; a control circuit including a DC voltage source connected to the electrodes in order to apply, to a pair of electrodes, DC voltage pulses, and in order to connect another high-impedance electrode; and a measurement circuit for measuring the potential of the electrodes and data representative of the current passing through at least one active electrode. The device further includes at least one base incorporating the control circuit and the measurement circuit, and a housing suitable for receiving an electrode assembly which includes at least one electrode of the series in a removable manner, so as to be able to connect or
(Continued)

disconnect the electrodes to/from the control circuit and to/from the measurement circuit.

8 Claims, 5 Drawing Sheets

(51) Int. Cl.

| | | |
|---|---|---|
| *A61N 2/06* | (2006.01) | |
| *A61B 5/0476* | (2006.01) | |
| *A61B 5/1495* | (2006.01) | |
| *A61B 5/053* | (2006.01) | |
| *A61B 90/98* | (2016.01) | |
| *A61B 5/00* | (2006.01) | |
| *A61B 5/1477* | (2006.01) | |
| *A61B 5/145* | (2006.01) | |

(52) U.S. Cl.
CPC .......... *A61B 5/0537* (2013.01); *A61B 5/1477* (2013.01); *A61B 90/98* (2016.02); *A61B 5/14517* (2013.01); *A61B 2560/028* (2013.01); *A61B 2560/0276* (2013.01); *A61B 2560/0443* (2013.01); *A61B 2562/0209* (2013.01); *A61B 2562/0271* (2013.01); *A61B 2562/043* (2013.01)

(58) Field of Classification Search
CPC ... A61B 5/1477; A61B 5/14517; A61B 90/98; A61B 5/0002; A61B 2562/043; A61B 2562/0271; A61B 2562/0209; A61B 5/1495; A61B 5/0537
See application file for complete search history.

(56) References Cited

U.S. PATENT DOCUMENTS

| | | | |
|---|---|---|---|
| 3,821,949 A | 7/1974 | Hartzell et al. | |
| 4,365,637 A | 12/1982 | Johnson | |
| 4,509,531 A | 4/1985 | Ward | |
| 4,690,152 A | 9/1987 | Juncosa | |
| 4,794,934 A | 1/1989 | Motoyama et al. | |
| 4,947,862 A * | 8/1990 | Kelly ................... | A61B 5/0537 600/547 |
| 5,293,113 A | 3/1994 | Beha et al. | |
| 5,307,817 A | 5/1994 | Guggenbuhl et al. | |
| 5,406,956 A | 4/1995 | Farwell | |
| 5,685,319 A | 11/1997 | Marett | |
| 5,771,261 A | 6/1998 | Anbar | |
| 5,782,884 A | 7/1998 | Stotts et al. | |
| 5,800,350 A | 9/1998 | Coppleson et al. | |
| 5,928,155 A | 7/1999 | Eggers et al. | |
| 6,175,752 B1 | 1/2001 | Say et al. | |
| 6,236,886 B1 | 5/2001 | Cherepenin et al. | |
| 6,299,583 B1 | 10/2001 | Eggers et al. | |
| 6,336,045 B1 | 1/2002 | Brooks | |
| 6,387,671 B1 * | 5/2002 | Rubinsky ................ | A61B 5/0536 435/173.1 |
| 6,473,641 B1 | 10/2002 | Kodama et al. | |
| 6,491,647 B1 | 12/2002 | Bridger et al. | |
| 6,512,949 B1 | 1/2003 | Combs et al. | |
| 6,577,893 B1 | 6/2003 | Besson et al. | |
| 6,577,897 B1 | 6/2003 | Shurubura et al. | |
| 6,633,777 B2 | 10/2003 | Szopinski | |
| 6,725,087 B1 | 4/2004 | Rubinsky et al. | |
| 6,807,442 B1 | 10/2004 | Myklebust et al. | |
| 6,871,084 B1 | 3/2005 | Kingsley et al. | |
| 7,103,481 B2 | 9/2006 | Negri | |
| 7,161,362 B2 | 1/2007 | Shambroom et al. | |
| 7,392,199 B2 | 6/2008 | Karlov et al. | |
| 7,474,917 B2 | 1/2009 | Jang et al. | |
| 7,477,937 B2 | 1/2009 | Iijima et al. | |
| 7,931,592 B2 | 4/2011 | Currie et al. | |
| 8,085,144 B2 | 12/2011 | Appelt et al. | |
| 8,655,443 B2 | 2/2014 | Brunswick et al. | |
| 8,918,170 B2 | 12/2014 | Brunswick et al. | |
| 8,934,954 B2 | 1/2015 | Brunswick et al. | |
| 8,965,497 B2 | 2/2015 | Tournefier et al. | |
| 2002/0107452 A1 | 8/2002 | Kwong | |
| 2003/0078482 A1 * | 4/2003 | Kenan ................... | A61B 5/0536 600/372 |
| 2004/0043247 A1 | 3/2004 | Lee et al. | |
| 2004/0128088 A1 | 7/2004 | Laletin et al. | |
| 2004/0158167 A1 | 8/2004 | Smith et al. | |
| 2005/0113650 A1 | 5/2005 | Pacione et al. | |
| 2005/0119534 A1 | 6/2005 | Trost et al. | |
| 2005/0245839 A1 | 11/2005 | Stivoric et al. | |
| 2006/0085049 A1 | 4/2006 | Cory et al. | |
| 2006/0127964 A1 | 6/2006 | Ford et al. | |
| 2007/0124176 A1 | 5/2007 | Jung et al. | |
| 2007/0178167 A1 | 8/2007 | Andrijauskas | |
| 2009/0054742 A1 | 2/2009 | Kaminska et al. | |
| 2009/0318779 A1 | 12/2009 | Tran | |
| 2009/0326407 A1 | 12/2009 | Tournefier et al. | |
| 2010/0081941 A1 | 4/2010 | Naghavi et al. | |
| 2010/0274113 A1 | 10/2010 | Brunswick et al. | |
| 2013/0053673 A1 | 2/2013 | Brunswick | |
| 2013/0053721 A1 | 2/2013 | Brunswick | |
| 2013/0204103 A1 | 8/2013 | Maarek | |
| 2014/0236077 A1 * | 8/2014 | Robertson ............ | A61B 5/0006 604/66 |
| 2015/0250404 A1 | 9/2015 | Albert | |

FOREIGN PATENT DOCUMENTS

| | | |
|---|---|---|
| WO | WO-00/19894 A1 | 4/2000 |
| WO | WO-2004/043247 A1 | 5/2004 |

OTHER PUBLICATIONS

Atkins, Peter, et al.; "Atkins' Physical Chemistry," Eighth Edition, 2006, pp. 1-1053.

Awad, Aymen A. et al.; "The Relationship Between the Photoplethysmographic Waveform and Systemic Vascular Resistance," Journal of Clinical Monitoring and Computing, vol. 21, No. 6, Oct. 17, 2007, pp. 365-372.

Brunswick, P., et al.; "Use of Ni electrodes chronoamperometry for improved diagnostics of diabetes and cardiac disease;" Proceedings of the 29th Annual International Conference of the IEEE EMBS, Lyon France, Aug. 23-26, 2007; pp. 4544-4547.

Chizmadzhev, Yuri A., et al.; "Electrical Properties of Skin at Moderate Voltages: Contribution of Appendageal Macropores," Biophysical Journal, vol. 74, Feb. 1998, pp. 843-856.

Cronin, Jane; Mathematics of Cell Electrophysiology, vol. 63, 1981, p. 23.

Gin, H., et al.; "Non-invasive and Quantitative Assessment of Sudomotor Function for Peripheral Diabetic Neuropathy Evaluation," Diabetes Metab, 2011, doi: 10.1016/j.diabet.2011.05.003, six pages.

Hubert, Dominique, et al.; "Abnormal electrochemical skin conductance in cystic fibrosis," Journal of Cystic Fibrosis, doi; 10:1016/j.jcf.2010.09.002, 2010, seven pages.

Khalfallah, K. et al.; "Noninvasive Galvanic Skin Sensor for Early Diagnosis of Sudomotor Dysfunction: Application to Diabetes," IEEE Sensors Journal, vol. 12, No. 3, Mar. 2012, pp. 456-463.

Li, Jin et al; "Computation of Cardiac Output by Pulse Wave Contour," IEEE, 2007, pp. 1088-1090.

Mayaudon, H. et al.; "A new simple method for assessing sudomotor function: Relevance in type 2 diabetes," Diabetes & Metabolism 36 (2010), Mar. 31, 2010, pp. 450-454.

Millasseau, Sandrine C. et al.; "Contour analysis of the photoplethysmographic pulse measured at the finger," Journal of Hypertension, vol. 24, No. 8, Aug. 2006, pp. 1449-1456.

Wang, L. et al.; "Noninvasive Cardiac Output Estimation Using a Novel Photoplethysmogram Index," 31st Annual International Conference of the IEEE EMBS, Minneapolis, MN, Sep. 2-6, 2009, pp. 1746-1749.

(56) References Cited

OTHER PUBLICATIONS

Gin, H., et al.; "Non-invasive and Quantitative Assessment of Sudomotor Function for Peripheral Diabetic Neuropathy Evaluation," Diabetes Metab, 2011, doi: 10.1016/j.diabet.2011.05.003, 6 pages.

Hubert, Dominique, et al.; "Abnormal electrochemical skin conductance in cystic fibrosis," Journal of Cystic Fibrosis, 2010, seven pages.

"DDFAO, Dépistage et Diagnosic Fonctionnel Assisté par Ordinateur (Computerized screening and functional diagnosis)," website—http://ms-tek.pagesperso-orange.fr/home_introduction.htm, Medical Screening Technologies Ltd (MS-Tek), published in 2004; 45 pages.

U.S. Appl. No. 14/424,704, filed Feb. 27, 2015, Kamel Khalfallah, Philippe Brunswick.

U.S. Appl. No. 14/553,544, filed Nov. 25, 2014, Philippe Brunswick, Nicolas Bocquet.

* cited by examiner

DEVICE FOR MEASURING ELECTROPHYSIOLOGICAL DATA WITH IMPROVED RELIABILITY

CROSS-REFERENCE TO RELATED APPLICATIONS

This application is a National Phase Entry of International Patent Application No. PCT/EP2015/077595, filed on Nov. 25, 2015, which claims priority to French Patent Application Serial No. 1461447, filed on Nov. 25, 2014, both of which are incorporated by reference herein.

TECHNICAL FIELD

The invention relates to the field of electrophysiological analysis of the human body, for example in order to detect pathologies. The invention is particularly applicable to the evaluation of the function of the human body.

BACKGROUND

Figure 1:
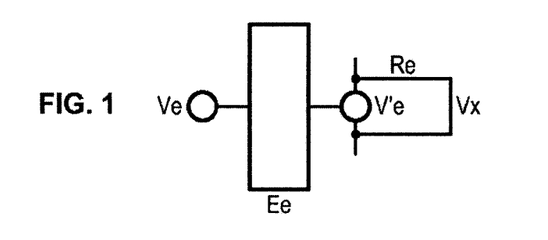
FIG. 1, already described, represents the electrical diagram of the positioning of an electrode on the skin.

The applicant has already proposed, for example in patent FR 2 912 893, then in the patents FR 2 994 819, FR 2 994 820, or FR 2 994 821, an electrophysiological analysis system comprising a series of electrodes intended to be positioned in different regions of the body of a patient, a DC voltage source adapted to generate adjustable DC voltage pulses, and a control circuit arranged to selectively connect a pair of so-called active electrodes to the source of Voltage electrodes, said active electrodes constituting an anode and a cathode, and for connecting at least one of the other high impedance electrodes. The voltage applied by the voltage source to the electrodes makes it possible to generate an electrophysiological current in the outer layer of the skin by electrochemical reaction at the level of the sweat glands, the study of certain characteristics of which may indicate certain pathological pathologies or predispositions. The sweat glands, of which a schematic electrical representation is given in FIG. 1, behave as a non-linear dipole, that is to say that the resistance $R_e$ (and therefore the conductance) of the sweat glands varies as a function of the difference of $V'_e - V_x$, where $V_x$ is the potential of the body, which is given by measuring the potential of the electrodes connected in high impedance, $V'_e$ is the voltage imposed on the gland by an electrode, $V_e$ is the Voltage applied or measured at the electrode, and $E_e = V_e - V'_e$ is the force against electromotive force or overvoltage of the electrode.

Figure 2A:
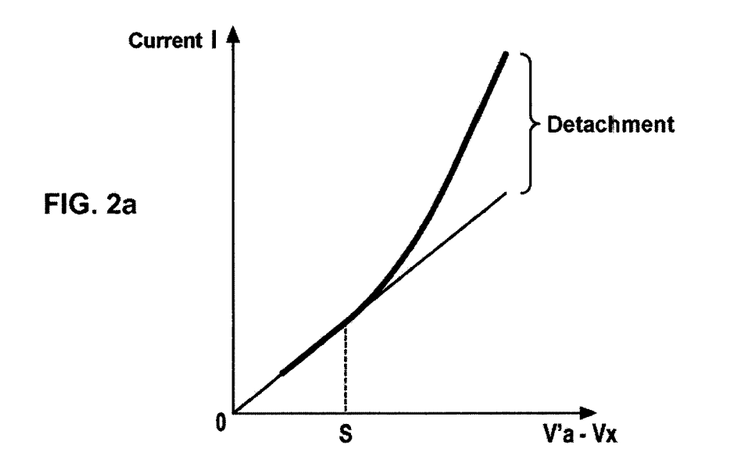
FIGS. 2a and 2b, already described, show respectively the evolution of the current and the conductance measured on a healthy individual as a function of the potential difference imposed on the skin.

The conductance of the sweat glands, or electrochemical conductance of the skin, is therefore the ratio between the current flowing through said glands and the potential difference to which they are subjected. However, this conductance varies not only as a function of the difference in potential applied to the sweat glands, but also as a function of the state of health of the individual. Thus, for example, with reference to FIG. 2a, the curve of the current passing through the eccrine glands is represented as a function of the potential difference imposed on the glands present in a healthy patient. There are two distinct sections: a first linear section, followed by a detachment and a second non-linear section.

Figure 2B:
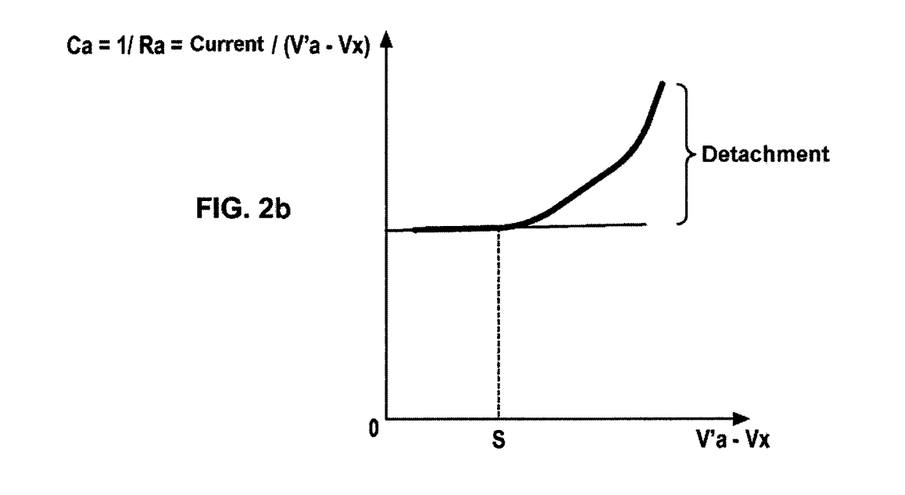

The detachment corresponds, in FIG. 2b, to a voltage threshold beyond which the conductance is increasing with the potential difference. On the other hand, this detachment may disappear in certain individuals suffering from pathologies, such as cystic fibrosis. This has been developed in the Applicant's patent application US-2013-0053673.

It is therefore interesting to measure the conductance for different potential differences imposed on the electrodes in different persons, to diagnose diseases in these persons, or several times in the same person, to monitor the course of a disease. However, the chemical reactions stimulated in the skin of an individual by the application of voltage to electrodes lead to oxidation and reduction reactions at the level of the electrodes themselves. The oxidation reactions cause the existence of an overvoltage at the level of the electrodes, having the effect of biasing the measurements of voltages at the level of the electrodes and therefore of degrading the quality of the electrochemical conductance measurements of the skin.

This problem has already been raised in patent application FR 1358780 by the Applicant. In this patent application a specific measurement protocol has been proposed to stabilize the overvoltage appearing on an electrode the time of a measurement in order to correct the data obtained. However, the overvoltage of an electrode can change over time and it is not sufficient to stabilize this overvoltage only for the time of a measurement. Indeed, it is not possible to compare data acquired in one or more persons if the overvoltage of the electrodes used to obtain the data has evolved.

SUMMARY

The purpose of the invention is to overcome the problem mentioned above. In particular, an object of the invention is to propose a device for recording electrophysiological data making it possible to reduce the variability of measurements caused by the overvoltage of the electrodes. Another object of the invention is to propose a device for recording electrophysiological data of reduced cost.

Regarding, the subject matter of the invention is a device for recording electrophysiological data comprising:
  a series of electrodes intended to be placed in contact with the skin of an individual,
  a control circuit comprising a DC voltage source and connected to the electrodes for selectively applying to a pair of so-called active electrodes of the series a DC square voltage and for connecting at least one other electrode of the high impedance series, and
  a circuit for measuring the potential of the electrodes of the series and data representative of the current flowing through at least one active electrode and,
the device being characterized in that it comprises at least one base integrating the control circuit and the measuring circuit,
and in that the base further comprises a housing adapted to removably receive an electrode assembly including at least one electrode of the series so as to selectively connect or disconnect the electrodes of the control circuit and the circuit of measurement.

Advantageously, but optionally, the device according to the invention may also comprise at least one of the following characteristics:
  the electrode assembly comprises an RFID tag and the base comprises an RFID reader, and wherein:
    the RFID tag comprises in memory a maximum number of uses, and a number of uses already done, and
    the RFID reader is adapted to read the maximum number of uses and to read and write in the memory of the RFID tag a number of uses already done.
  The electrodes are made of stainless steel and have a thickness of between 0.5 and 1.5 mm, said thickness being determined as a function of a maximum number of uses of the electrodes.

The base further comprises an infrared sensor adapted to measure the temperature of at least one electrode of the electrode assembly.

The device comprises a second base, electrically connected to the first and having a housing adapted to removably receive a second assembly of electrodes, and the series of electrodes comprises four electrodes distributed in pairs in the electrode assemblies so that an individual can position his hands on the two electrodes of a first assembly and his feet on the two electrodes of the second assembly.

An electrode assembly comprises two electrodes and an electronic circuit, adapted to selectively connect the electrodes of a same assembly:
  or by a branch in high impedance,
  or by a resistor of determined value.

The subject of the invention is also an electrophysiological analysis system comprising:
  A data acquisition device according to the preceding description, and
  A processing unit adapted to communicate with the base of the device comprising the control circuit and the measurement circuit and for determining from the measured data at least one electrochemical conductance value of the skin.

Advantageously, but optionally, the electrophysiological analysis system presented also comprises at least one of the following characteristics:
  The processing unit is remote from the data retrieval device and adapted to communicate therewith by a wireless communication mode as Bluetooth or Wi-Fi.
  The processing unit is further adapted to:
    test the operation of the data reading device, and, if the test result is positive,
    to command the base to trigger a measurement protocol.

The subject of the invention is also an electrophysiological analysis method, implemented by a system according to the preceding description, comprising the steps consisting in:
  testing the operation of the data reading device, said test comprising at least one of the following group:
    temperature test of the electrodes,
    electrical conductivity test of the electrodes,
    test of the possibility of using the electrodes with respect to a maximum number of uses and
  if the result of the functional test is positive, implement an electrophysiological analysis protocol, comprising:
    the application to a pair of active electrodes of the DC square voltage and the connection of at least one other high impedance electrode,
    the reading of data representative of the current flowing through at least one active electrode and of the potential of at least one electrode;
    on the basis of said data, determining at least one electrochemical conductance value of the skin.

Advantageously, but optionally, the electrophysiological analysis method according to the invention may also comprise at least one of the following characteristics:
  The electrode temperature test comprises measuring the temperature of at least one electrode and producing a positive result if the temperature is between 18 and 35° C.
  The method being implemented by a system in which an electrode assembly comprises an RFID chip comprising in memory a maximum number of uses and a number of uses already carried out,
  the test for the possibility of using the electrodes comprises:
    reading the maximum number of uses and the number of uses already done, and
    producing a positive test result if the number of uses already done is strictly lower than the maximum number of uses.
  the method being implemented in a system in which a assembly of electrodes comprises two electrodes and an electronic circuit adapted selectively to connect the electrodes with a resistor of determined value,
  the electrical conductivity test of the electrodes comprises:
    the application, to an electrode of an assembly, of a known voltage,
    measuring the potential of the other electrode of the assembly,
    comparing the measured potential with a theoretical potential obtained from the value of the resistance, and
    the production of a positive test result if a difference between the measured potential and the theoretical potential is less than a determined threshold.

The proposed device comprises removable electrodes, making it possible to renew these electrodes after a number of uses. In this way, the variability of the electrode overvoltage can be limited by limiting the number of uses of the electrodes to an acceptable level. Moreover, since all of the control electronics of the device are integrated into the base of the electrodes, it results that the removable electrode assemblies are less expensive and can be easily replaced. The base can be preserved without any problem of wear.

BRIEF DESCRIPTION OF THE DRAWINGS

Other characteristics, objects and advantages of the present invention will appear on reading the detailed description which follows, with regard to the appended figures, given as non-limiting examples and in which.

DETAILED DESCRIPTION

Electrophysiological Data Recording Device

Figure 3A:
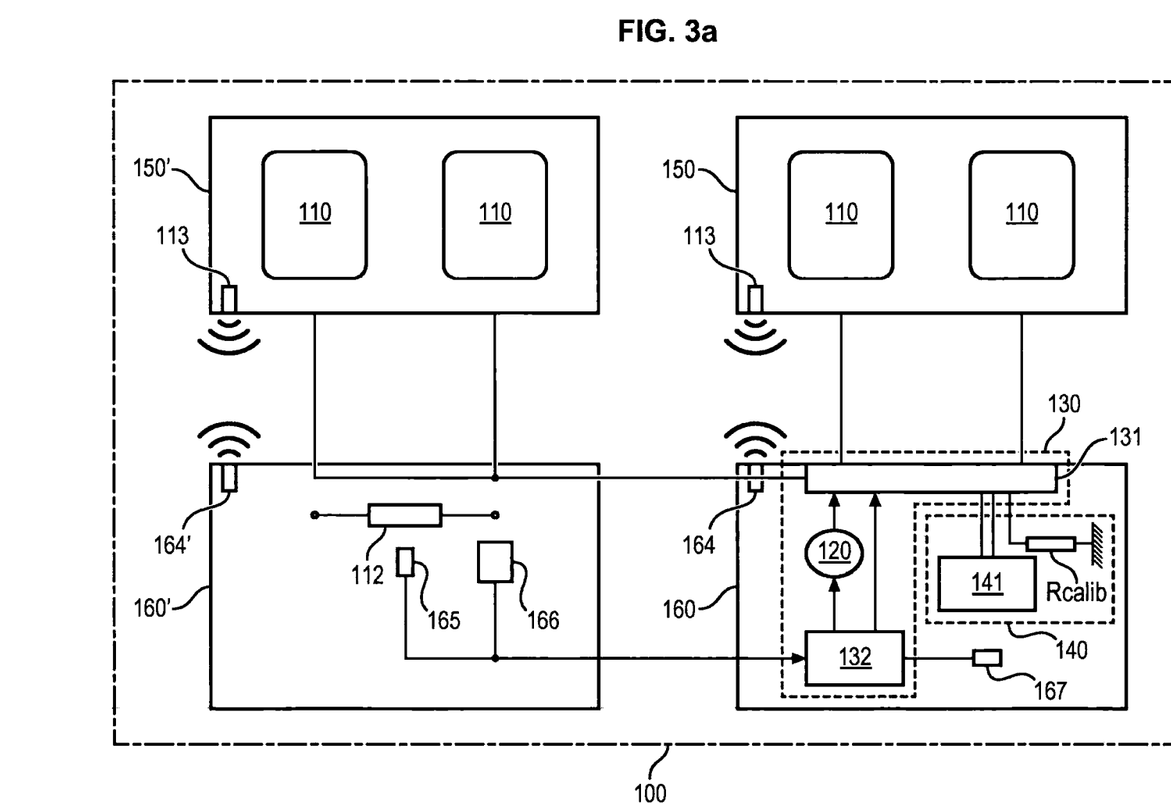
FIGS. 3a and 3b show schematically an electrophysiological data recording device and an analysis system according to an embodiment of the invention.

With reference to FIG. 3a, a device 100 for recording electrophysiological data has been represented schematically. This device 100 comprises a plurality of electrodes 110, preferably four electrodes. The electrodes 110 advantageously comprise two electrodes intended to be placed in contact with the two hands of an individual, and two electrodes intended to be placed in contact with the two feet of an individual.

Regarding, each electrode has an area sufficient to cover the entire palm of the hand or the entire soles of the foot of an individual, for example an area greater than 100 cm$^2$, or even greater than 150 cm$^2$. To establish contact between the skin of an individual and the electrodes, the individual stands on the electrodes intended to be placed in contact with the feet and places his hands on the other two electrodes. The electrodes 110 are advantageously made of stainless steel because this material is hypoallergenic and in addition it allows a good repeatability of the measurements.

The device 100 also comprises an electrical control circuit 130, comprising a DC voltage source 120, adapted to generate a DC square voltage and advantageously constant. The voltage delivered by the source is preferably between 0 and 10 V, advantageously between 0 and 4 V. The electrical circuit 130 comprising the source 120 is connected to the electrodes 110 so as to be able to selectively connect a pair of electrodes, forming an anode and a cathode, to the DC voltage source so that the latter applies thereto DC square voltage. These electrodes are said to be "active".

The other electrodes are then connected in high impedance, and make it possible to measure the potential reached by the body. They are called "passive" electrodes. In order to be able to connect one pair chosen from active electrodes and the other from high-impedance, the circuit 130 advantageously comprises a switch 131 establishing the desired connections between the electrodes and the voltage source.

The electric circuit 130 advantageously also comprises a controller 132 of the voltage source 120. The controller drives the source 120 so that the latter supplies to the electrode connected as anode the DC square voltage of a fixed duration, at a determined potential level, and at a determined interval for the implementation of a measuring method described hereinafter.

The device 100 also comprises a measuring circuit 140, arranged to measure the potentials of the passive electrodes, and to measure the current between the active electrodes. In this regard, the measuring circuit 140 advantageously comprises a measuring resistor $R_{calib}$ connected in series between the cathode and a reference voltage, for example the ground, and a measuring device 141, for example a voltmeter, adapted to measure the potentials of the passive electrodes and the voltage across the measuring resistor, so, advantageously, the only potential of the electrode connected as a cathode if the resistor is connected to ground. The current through the cathode is determined by this device 141 by measuring the voltage across measuring resistor and dividing this voltage by the value of the resistance. Advantageously, but optionally, the measuring circuit 140 may further comprise another measuring resistor (not shown) arranged in series between the DC voltage source and the anode, in order to detect, if needed, a leakage of the current imposed by the source of voltage or the presence of an additional current imposed on the body by another device, as proposed in the patent FR 1258036 of the Applicant.

Figure 4:
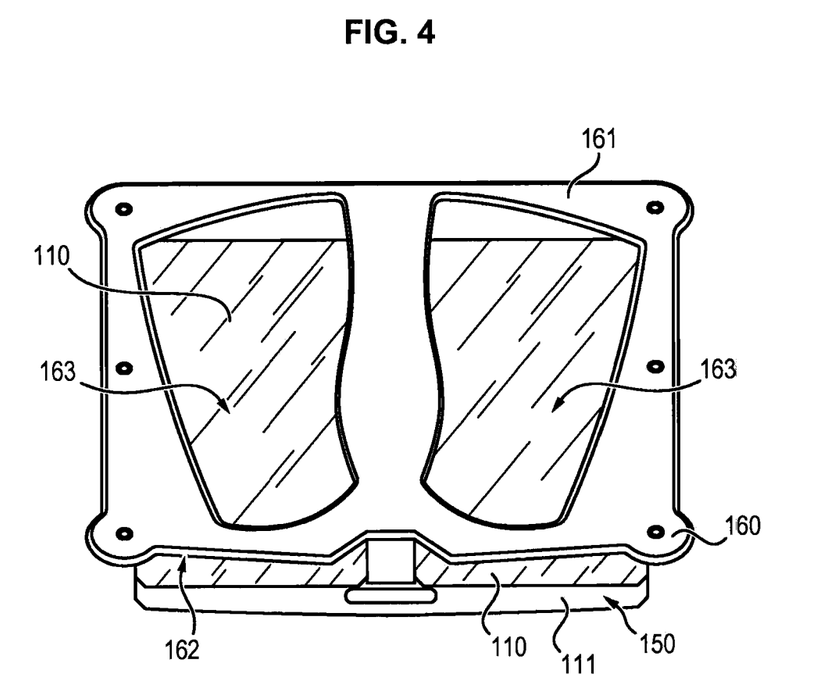
FIG. 4 shows a partial view of a device for recording electrophysiological data.

As schematically represented in FIG. 3a and in FIG. 4, the electrodes 110 of the device 100 are removable. In this way, when electrodes are worn, they can be replaced by new ones. Worn electrodes can be discarded or recycled.

The device 100 comprises at least one electrode assembly 150 which comprises at least one and preferably two electrodes 110 mounted on an electrically insulating support 111 in order to avoid short-circuiting the electrodes. Advantageously, as indicated above, the device 100 comprises two electrodes 110 for the hands, and two for the feet. In this case, it then comprises two assemblies of electrodes 150, 150', a first assembly comprising the two electrodes intended to be in contact with the feet, and the second comprising the two electrodes intended to be in contact with the hands.

In each electrode assembly, the electrodes are positioned to provide comfortable contact for a user. Thus, the electrodes intended to be in contact with the feet are preferably spaced from 0 to 30 cm edge to edge, and preferably from 10 to 20 cm, corresponding to a comfortable average distance from the feet. Similarly, the electrodes intended to be in contact with the hands are preferably spaced from 0 to 30 cm, and preferably from 10 to 20 cm.

The support of the electrodes may advantageously be made of plastic. The electrodes may be attached thereto, removably or not, for example by snap-fastening, or embedded, or bonded. Preferably, each electrode assembly has the shape of a rectangular parallelepiped with a thickness of less than 5 cm, and preferably less than 1 cm.

Advantageously, the base 160 comprises an electronic circuit 112 (shown only on the second base 160 for clarity), for example a multiplexer, adapted to selectively connect the electrodes 110 of a same assembly:

Either by a branch in high impedance, to prevent any current flow between the electrodes, when it is desired to implement measurements of electrochemical conductance of the skin, Or by a resistance of determined value, making it possible to carry out a conductivity test of the electrodes, described hereinafter with reference to FIG. 5.

On the other hand, the device 100 comprises at least one base 160, adapted to receive in a removable manner an assembly of electrodes 150. In this respect, the base advantageously comprises a housing 161 whose shape corresponds to that of the electrode assembly, his housing 161 opening onto the outside of the base 160 by a slot 162 through which the electrode assembly can be inserted and removed. In addition, the base further comprises at least one through-opening 163 disposed facing each electrode 110 to allow contact with the electrode across the wall of the base. Thus, the openings advantageously have a surface area greater than 100 or even 150 cm² so as not to impede the positioning of a foot or a hand of an individual on an electrode.

In addition, the base 160 advantageously comprises the majority of the electronics of the device 100, in order to limit the cost of the electrode assembly 150. Therefore, the control circuit 130 and the measuring circuit 150 are all disposed in the base or bases 160. As can be seen in FIG. 3a, in the preferred case in which the device 100 comprises two assemblies of electrodes 150, 150', it also comprises two bases 160, 160'. In this case, the second base 160' is advantageously connected to the first by a wire connection.

It can thus constitute an intermediary in the connection between the switch 131 and the electrodes 110 of the corresponding electrode assembly 150'. In this case also, each base 160 160' comprises an electronic circuit 112 adapted to connect the corresponding electrodes 110 in high impedance or by a resistor to carry out the conductivity test of the electrodes.

In addition, each base 160 advantageously comprises an electrical connection with the electrodes 110 to allow the application of the voltage delivered by the source 120 to the electrodes. For this purpose, each base 160 comprises as many electrical contacts (not shown) as electrodes in an electrode assembly each electrical contact coming into contact with an electrode when the electrode assembly is inserted into position in the electrode assembly housing 161 of the corresponding base. Thus, when the electrode assembly is removed from the housing 161, the contact is disconnected and the electrodes are disconnected from the control circuit, in particular the voltage source, and the measuring circuit.

The structure of the data acquisition device 100 therefore makes it possible to use renewable electrodes at low cost, since only the part in contact with the skin of the individual must be changed as a function of its wear. Since all the control and measurement electronics are housed in the base (s) 160, it is not changed at the time of renewal of the electrodes. In order to further limit the cost of an assembly of electrodes, the electrodes advantageously have a thickness suited to a maximum number of uses. For example, if it is desired to renew the electrodes after a hundred measurements, the electrodes may have a thickness of approximately 0.8 mm. If it is desired to renew the electrodes after about a thousand measurements, the thickness of the electrodes may be about 1.5 mm. Moreover, this solution makes it possible to add functionalities to the device 100.

It is preferable to control the number of uses of the electrodes to ensure that the electrodes are renewed before the overvoltage of the electrodes evolves too much. For example, it may be decided to replace the electrodes after 1000, preferably after 500, or more preferably after 100 uses.

To ensure that the electrodes are replaced, each assembly of electrodes preferably comprises an RFID tag 113. Advantageously, this label can be embedded in the support part, to prevent its removal and replacement. The RFID tag 152 comprises in a manner known per se a memory and an antenna adapted to communicate the information contained in the memory. The RFID tag may be of the passive type, in which case the energy of the antenna is communicated by a reader, or of active type, in which case the label also includes a source of energy feeding the antenna. Advantageously, it is of the passive type for limiting the price and the number of electronic components contained in the electrode assembly 150. Advantageously, the memory of the RFID tag comprises the following two fields:

Maximum number of uses of the electrode assembly, and
Number of uses of the electrode assembly.

The base 160, 160' corresponding to the electrode assembly is advantageously provided with an RFID tag reader 164, 164'. This reader is adapted to read the first field and to read and write the second field. In order to verify that the electrode assembly is still usable, before each measurement method, the reader 164, 164' reads the two fields and compares the number of uses past with the maximum number of uses of the assembly of electrodes.

If the number of past uses is strictly lower than the maximum number of uses, the reader 164, 164' sends a favorable signal to the control circuit 130 and then increments the number of uses made by 1. If the number of uses done is greater than or equal to the maximum number of uses, the reader 164, 164' sends an unfavorable signal to the control circuit 130 preventing the implementation of a measurement method. This signal may indicate to a user the need to renew the electrode assembly.

The base receiving the assembly of electrodes dedicated to being placed in contact with the feet of an individual advantageously comprises a weight sensor 165. The weight sensor 165 enables the weight of the individual to be recorded before the measurement to record this information with the data on the electrochemical conductance of the skin of the individual.

In addition, each base advantageously comprises a thermal sensor 166, preferably an infrared sensor adapted to measure, preferably before the electrochemical conductance of the skin, the temperature of at least one electrode 110 (sensor shown only on the base 160' to clarify the figures). Depending on the temperature of the electrodes, the thermal sensor 166 can prevent the start of a measurement protocol. Indeed, it has been found that when contact with cold electrodes, a phenomenon of vasoconstriction limits the electrochemical phenomena in the ion channels of the sweat glands and degrades the conductance measurements of the skin.

It is therefore preferable for the electrodes to have a temperature greater than or equal to 18° C. in order to start the measurement. Furthermore, in order to ensure the correct operation of the control electronics, it is preferable that the electrodes are not too hot. The temperature of the electrodes 110 must therefore lie in a range between 18° C. and 35° C. in order to obtain a measurement under good conditions. The thermal sensor 166 advantageously communicates with the control circuit 130, which blocks the conductance measurement if the temperature of the electrodes is outside this range.

Finally, at least one base 160 comprises a source of energy 167, advantageously a battery, in order to be self-sufficient in energy and to be easily deployable in different places. This energy source is advantageously adapted to provide the energy required for a high number of uses, which is greater than several full uses of electrode assemblies, for example several thousand uses of the device.

Electrophysiological Analysis System

Figure 3B:
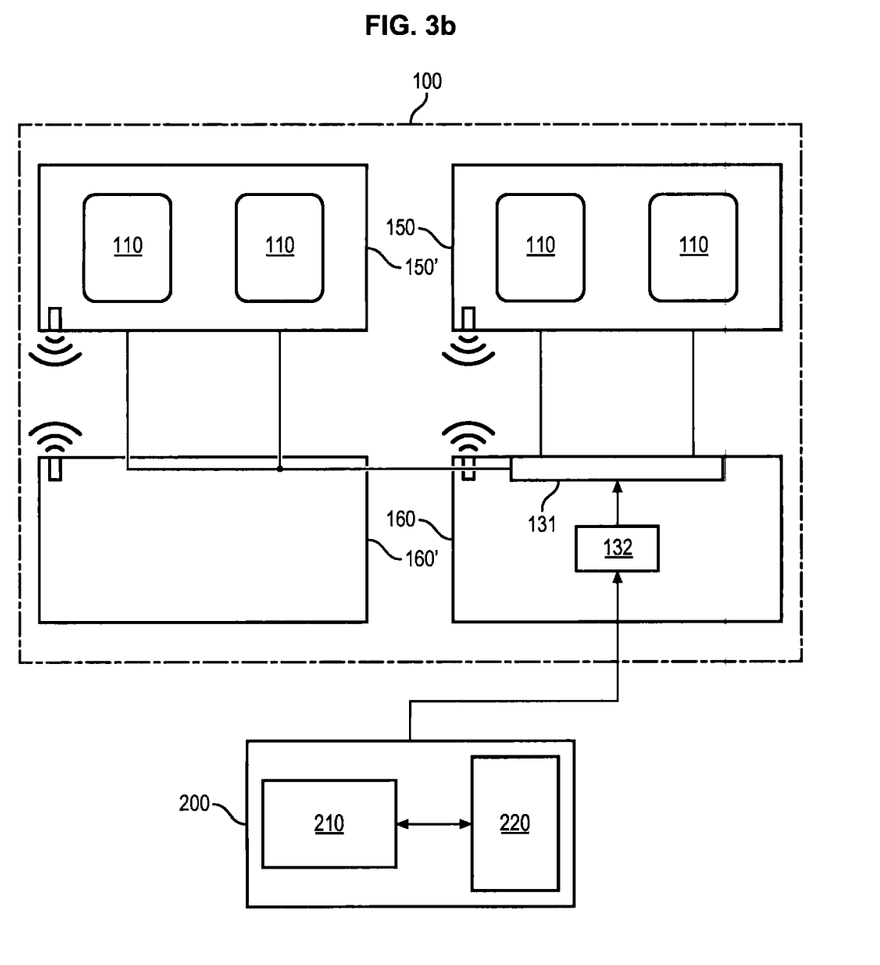

The device 100 described above is advantageously integrated into an electrophysiological analysis system 200 for the implementation of a method for measuring an electrochemical conductance of the skin of an individual. The analysis system is shown in FIG. 3*b*, with certain details of the device 100 being omitted for clarity. In addition to the device 100, the analysis system 200 comprises a processing unit 210. This processing unit is advantageously an entity distinct from the base (s). For example, it may be a portable tablet or a computer, to which the device 100 is connected. In this regard, the connection may be wired or wireless. According to a preferred embodiment of the invention, the connection between the processing unit 210 and the device 100 is implemented by Bluetooth or Wi-Fi. More specifically, the processing unit 210 comprises processing means, for example a processor, adapted to communicate with the control circuit 130 in order to perform certain functions. Advantageously, the processing unit drives the control circuit 130 to start the execution of a measurement protocol, and then to recover the values of potentials measured by the measuring circuit 140.

On the basis of the voltage values of the electrodes connected in high impedance and the value of the potential difference across the measuring resistor for each potential value applied to the anode, the processing unit calculates the current between the electrodes and then the electrochemical conductance of the skin for each potential value, this conductance being provided by the ratio between the current between the active electrodes and the potential reached by the body, corresponding to the potential of the high impedance electrodes. The processing unit may also produce one or more curves representing the electrochemical conductance of the skin as a function of the potential applied to the anode and those for several sequences of measurements with different electrodes connected as anode. The processing unit 210 may further load older information about the same individual, or analogous statistical data on a healthy population of people for comparison.

Furthermore, the processing unit may control the control circuit 130 to carry out preliminary tests to verify the correct functioning of the device. For example, a temperature test or an electrode conductivity test. The processing unit advantageously recovers the following information:

The weight value measured by the sensor 163, this value being able to be recorded in a database (not shown) with other information concerning the individual.

Temperature value, for example in a case where the measurement has been blocked and it is desired to know the reason for this blocking The value of an electrode voltage measured in the context of a conductivity test, in the case where the measurement has been blocked following the implementation of the test.

Number of uses already done of electrodes assemblies.

Depending on the information received, the processing unit 210 may supplement a database of measured information concerning the individual.

Finally, the system advantageously comprises a display 220 connected to the processing unit. The display shows:
Measured data: electrochemical conductance of the skin of an individual, weight of the individual, previously recorded data for the individual or other persons, Information about the system:
  Prohibition, where appropriate, of the implementation of a protocol of measurement, and reason for the prohibition,
  Indication of the temperature of the electrodes
  Indication of a number of uses of the electrode assemblies,
  Indication of a measured electrode voltage value in the context of a conductivity test, etc.

Electrophysiological Analysis

Figure 5:
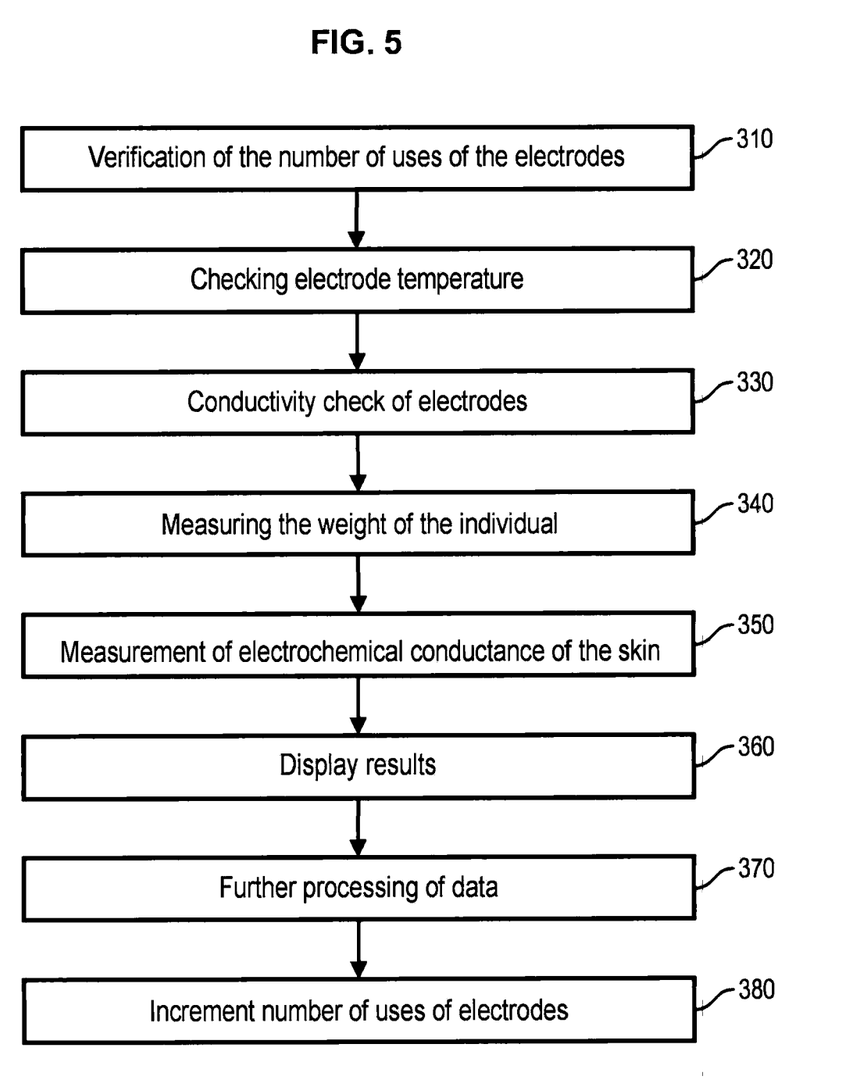
FIG. 5 shows the main steps of an electrophysiological analysis method according to one embodiment.

With reference to FIG. 5, the main steps of an electrophysiological analysis method implemented by a system 200 have been represented schematically. This method advantageously comprises preliminary verification steps of the system, before an individual puts his hands or feet in contact with the electrodes. These preliminary steps are advantageously controlled by the processing unit 210 to the control circuit 130, which relays to the sensors concerned.

A first preliminary step 310 comprises a verification that the maximum number of uses of the electrode assemblies is respected. This step is advantageously carried out before any measurement of conductance of the skin. It is implemented by the following algorithm:

For each assembly comprising a base 160 and an electrode assembly 150, the reader 164 of the base reads the maximum possible number of uses of the assembly and the current number of uses of the assembly.

If the current number is strictly less than the maximum number, the reader 164 communicates a positive signal to the control circuit 130, this signal authorizing the implementation of a measurement protocol, If the current number is greater than or equal to the maximum number, the reader 164 communicates a negative signal to the control circuit 130, preventing the implementation of the measurement protocol. In this case, the control circuit 130 communicates to the processing unit 210 a message indicating the cause of the prohibition, which can be displayed safely on the display 220.

A second preliminary step 320 comprises a check of the temperature of the electrodes. This step is advantageously carried out before any measurement of conductance of the skin. It is implemented as follows:

For each assembly comprising a base and an assembly of electrodes, the temperature sensor measures the temperature of the electrodes 110, If the temperature is within the acceptable range, for example between 18° C. and 35° C., the temperature sensor communicates a positive signal to the control circuit 130, this signal authorizing the implementation of a measurement protocol. The sensor 166 can also communicate the temperature value to the control circuit 130, which can transmit it to the processing unit 210, possibly for display.

If the temperature is outside the acceptable range, the temperature sensor 166 communicates a negative signal to the control circuit 130, preventing the implementation of the measurement protocol. It also communicates the temperature, this temperature being advantageously transmitted by the control circuit 130 to the processing unit 210 and displayed on the display 220.

A third preliminary step 330 comprises a verification of the conductivity of the electrodes. This step can be implemented occasionally, to check the correct functioning of the electrode assemblies, for example every ten measurements. This step is implemented as follows:

The control circuit 130 connects the two electrodes 110 of one and the same assembly 150 so that one is connected in anode and the other in cathode and controls the electronic circuit 112 to connect these two electrodes by the resistance of value known.

The controller of the control circuit 130 drives the voltage source 120 to apply a voltage of known value to the anode.

Since the resistance between the electrodes is known, and the measuring resistor of the measuring circuit 140 is also known, a voltage divider bridge is made in this way. It is therefore possible to determine, as a function of the values of the resistors, the expected value of the voltage at the cathode.

The measuring circuit 140 detects the voltage at the cathode and compares this value with the expected value.

If there is a difference between the two values exceeding a given threshold (for example in percentage), the measuring circuit 140 communicates a negative signal to the control circuit 130, prohibiting the implementation of the measurement protocol. Advantageously, it also communicates the value of the voltage to the cathode, this value being able to be transmitted to the processing unit 210 and to the display 220.

If there is no difference or the difference is less than the threshold, the measuring circuit 140 communicates a positive signal to the control circuit 130, allowing the implementation of the measurement protocol.

Once these preliminary steps have been implemented, an individual can mount on the first base 160 by positioning his feet on the electrodes 110. A step 340 for measuring the weight of the individual can then be implemented by the weight sensor 165. The measured value is advantageously communicated to the control circuit 130, then to the processing unit and to the display 220.

Next, the individual can position his hands on the electrodes 110 inserted in the second base 160', in order to carry out the step of measuring the electrochemical conductance of the skin 350. The processing unit 210 then controls the control circuit 130 for:

Connect an electrode to the voltage source (then anode), an electrode to ground via the measuring resistor (cathode), and the other electrodes in high impedance, Pilot the voltage source to deliver to the anode a series of positive DC voltage slots. Advantageously, the series comprises at least 10 slots, and preferably at least 15 slots. The slots advantageously have a strictly increasing or strictly decreasing tension on the series. For example, the voltage may vary between 0.5 and 1.5 V, for example of the order of 1 V for the lowest voltage slot, up to 3.5 to 4.5 V, for example 4 V, For the highest voltage slot. The slots may have a duration of between 1 and 2 seconds, preferably equal to 1 s. The first slot may, however, be longer, in order to stabilize the anode overvoltage during measurement time. This slot can last from 5 to 10 seconds, for example about 8 seconds.

Control the measuring circuit 140 to record, at each slot:
The voltage at the cathode, with the value of the measuring resistor, makes it possible to deduce the intensity of the current between the active electrodes
The potential of the electrodes connected in high impedance, corresponding to the potential of the body.

Once the series of measurements have been carried out, the processing unit 210 recovers the voltage values and determines, for each voltage applied to the anode, the value of the electrochemical conductance of the skin as the ratio between the intensity of the current between the active electrodes and the potential of the body. This step is advantageously followed by a step 360 of displaying the results on the display. Optionally, a data processing step 370 can also be implemented to calculate the ratio or differences between several values of electrochemical conductance of the skin, to make comparisons with respect to other measurements, and the like. Finally, at the end of the measurement, the readers 164 of the bases increment 380 by 1 the number of uses of the electrode assemblies.

The invention claimed is:

1. An electrophysiological data reading device comprising:
   a series of electrodes adapted for placement in contact with skin of an individual;
   a control circuit comprising a DC voltage source, the control circuit being connected to the electrodes and operably selectively applying an active pair of the electrodes with a DC square voltage, and the control circuit operably connecting at least one other electrode of a high impedance series;
   a measuring circuit operably measuring a potential of the electrodes of the series and a current flowing through at least one of the active electrodes;
   a first base integrating the control circuit and the measuring circuit, and the first base further comprises a housing adapted to removably receive a first electrode assembly including at least one of the electrodes of the series so as to selectively connect or disconnect the electrodes of the series and the measuring circuit;
   wherein the first electrode assembly comprises an RFID tag and the first base comprises an RFID reader;
   wherein the RFID tag comprises in memory a maximum number of uses, and a number of uses already done; and
   wherein the RFID reader is adapted to read the maximum number of uses and to read and write from the memory of the RFID tag a number of uses already done.

2. The electrophysiological data reading device according to claim 1, wherein the electrodes are made of stainless steel and have a thickness of between 0.5 and 1.5 mm, the thickness being determined in function of a maximum number of uses of the electrodes.

3. The electrophysiological data reading device according to claim 1, comprising:
   a second base electrically connected to the first base and having a suitable housing adapted to removably receive a second assembly of electrodes; and
   the series of electrodes comprises four electrodes distributed in pairs in the first electrode assembly and the second electrode assembly so that an individual can position his hands on a pair of electrodes of the first electrode assembly and position his feet on a pair of electrodes of the second electrode assembly.

4. The electrophysiological data recording device according to claim 1, wherein the first electrode assembly comprises two electrodes and an electronic circuit adapted to selectively connect the electrodes of the first assembly:
   by a branch in high impedance; and
   by a resistance of determined value.

5. An electrophysiological data reading device comprising:
   a series of electrodes adapted for placement in contact with skin of an individual;
   a control circuit comprising a DC voltage source, the control circuit being connected to the electrodes and operably selectively applying an active pair of the electrodes with a DC square voltage, and the control circuit operably connecting at least one other electrode of a high impedance series;
   a measuring circuit operably measuring a potential of the electrodes of the series and a current flowing through at east one of the active electrodes;
   a first base integrating the control circuit and the measuring circuit, and the first base further comprises a housing adapted to removably receive a first electrode assembly including at least one of the electrodes of the series so as to selectively connect or disconnect the electrodes of the series and the measuring circuit;
   wherein the first base further comprises an infrared sensor adapted to measure the temperature of at least one electrode of the first electrode assembly.

6. An electrophysiological analysis method implemented by a system in which an electrode assembly comprises an RFID chip having in memory a maximum number of uses and a number of uses already done, the method comprising:
   (a) testing a usability of electrodes, the testing comprising reading the maximum number of uses and the number of uses already done, and producing a positive test result whenever the number of uses of the electrodes already done is strictly lower than the maximum number of uses;
   (b) whenever the positive test is produced, implementing an electrophysiological analysis protocol comprising:
      (i) applying to an active pair of the electrodes a DC square voltage and connecting at least one other high impedance electrode;
      (ii) reading of a current flowing through at least one of the active electrodes and of a potential of at least one of the electrodes; and
      (iii) on the basis of the data, determining at least one electrochemical conductance value of a patient's skin.

7. The electrophysiological analysis method according to claim 6, wherein the temperature test of the electrodes comprises measuring the temperature of at least one of the electrodes and producing a positive result whenever the temperature is between 18 and 35° C.

8. The electrophysiological analysis method according to claim 6, implemented in a system in which an electrode assembly comprises two of the electrodes and a selectively connectable electronic circuit including the electrodes with a resistor of determined value;

the electrical conductivity test of the electrodes being employed comprising:
applying to one of the electrodes of the assembly, a known voltage;
measuring a potential of the other electrode of the assembly;
comparing the measured potential with a theoretical potential obtained from a value of resistance; and
producing a positive test result whenever a difference between the measured potential and the theoretical potential is less than a determined threshold.

* * * * *